US00PP31123P2

(12) United States Plant Patent
Vandenberg

(10) Patent No.: US PP31,123 P2
(45) Date of Patent: Nov. 26, 2019

(54) ***HIBISCUS* PLANT NAMED 'FIRE WIND'**

(50) Latin Name: *Hibiscus rosa-sinensis*
Varietal Denomination: Fire Wind

(71) Applicant: Cornelis P. Vandenberg, Fort Myers, FL (US)

(72) Inventor: Cornelis P. Vandenberg, Fort Myers, FL (US)

(73) Assignee: Aris Horticulture, Inc., Barberton, OH (US)

( * ) Notice: Subject to any disclaimer, the term of this patent is extended or adjusted under 35 U.S.C. 154(b) by 0 days.

(21) Appl. No.: 15/999,915

(22) Filed: Aug. 29, 2018

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

*Primary Examiner* — June Hwu
(74) *Attorney, Agent, or Firm* — C. A. Whealy

(57) ABSTRACT

A new and distinct cultivar of *Hibiscus* plant named 'Fire Wind', characterized by its semi-upright, uniformly mounded plant habit appropriate for container production; freely branching habit, dense and bushy appearance; glossy dark green-colored leaves; uniform, freely and early flowering habit; large bright red-colored flowers with dark red-colored centers; and good postproduction and garden performance.

2 Drawing Sheets

Botanical designation: *Hibiscus rosa-sinensis.*
Cultivar denomination: 'FIRE WIND'.

BACKGROUND OF THE INVENTION

The present invention relates to a new and distinct *Hibiscus* plant, botanically known as *Hibiscus rosa-sinensis* and hereinafter referred to by the name 'Fire Wind'.

The new *Hibiscus* plant is a product of a planned breeding program conducted by the Inventor in Alva, Fla. The objective of the breeding program is to create new freely-branching *Hibiscus* plants with a dense, uniform and compact plant habit appropriate for container production, early and uniform flowering habit, numerous flowers per lateral branch, desirable flower color and good garden performance.

The new *Hibiscus* plant originated from a cross-pollination made by the Inventor in Alva, Fla. in 2009 of *Hibiscus rosa-sinensis* 'Largo Breeze', disclosed in U.S. Plant Pat. No. 12,869, as the female, or seed, parent with a proprietary selection of *Hibiscus rosa-sinensis* identified as code number 2691, not patented, as the male, or pollen, parent. The new *Hibiscus* plant was discovered and selected by the Inventor as a single flowering plant within the progeny of the stated cross-pollination in a controlled greenhouse environment in Alva, Fla. on Jul. 16, 2012.

Asexual reproduction of the new *Hibiscus* plant by vegetative terminal cuttings in a controlled greenhouse environment in Alva, Fla. since September, 2012 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Fire Wind'. These characteristics in combination distinguish 'Fire Wind' as a new and distinct *Hibiscus* plant:

1. Semi-upright, uniformly mounded plant habit appropriate for container production.
2. Freely branching habit, dense and bushy appearance.
3. Glossy dark green-colored leaves.
4. Uniform, freely and early flowering habit.
5. Large bright red-colored flowers with dark red-colored centers.
6. Good postproduction and garden performance.

Plants of the new *Hibiscus* can be compared to plants of the female parent, 'Largo Breeze'. Plants of the new *Hibiscus* differ primarily from plants of 'Largo Breeze' in the following characteristics:

1. Plants of the new *Hibiscus* are more uniform in plant habit than plants of 'Largo Breeze'.
2. Plants of the new *Hibiscus* are more uniform in flowering habit than plants of 'Largo Breeze'.
3. Plants of the new *Hibiscus* and 'Largo Breeze' differ in flower color as plants of 'Largo Breeze' have orange-colored flowers.

Plants of the new *Hibiscus* can be compared to plants of the male parent selection. Plants of the new *Hibiscus* differ primarily from plants of the male parent selection in the following characteristics:

1. Plants of the new *Hibiscus* are more upright than and not as outwardly spreading as plants of the male parent selection.
2. Plants of the new *Hibiscus* are more freely flowering than plants of the male parent selection.

Plants of the new *Hibiscus* can be compared to plants of the *Hibiscus rosa-sinensis* 'Antigua Wind', disclosed in U.S. Plant Pat. No. 23,656. In side-by-side comparisons plants of the new *Hibiscus* differ from plants of 'Antigua Wind' in the following characteristics:

1. Plants of the new *Hibiscus* are more vigorous than plants of 'Antigua Wind'.
2. Plants of the new *Hibiscus* are more uniform in plant habit than plants of 'Antigua Wind'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Fire Wind' grown in a container.

The photograph on the second sheet comprises a close-up view of a typical flowering plant of 'Fire Wind'.

DETAILED BOTANICAL DESCRIPTION

The aforementioned photographs and following observations, measurements and values describe plants grown during the summer in 20-cm containers in a polyethylene-covered greenhouse in Alva, Fla. and in an outdoor nursery in Fort Worth, Tex. under cultural practices which closely approximate commercial *Hibiscus* production. During the production of the plants, day temperatures ranged from 21° C. to 35° C., night temperatures ranged from 12° C. to 21° C. and light levels ranged from 5,000 to 8,000 foot-candles. Plants were pinched three times and were ten months old when the photographs and the description were taken. In the description, color references are made to The Royal Horticultural Society Colour Chart, 2007 Edition, except where general terms of ordinary dictionary significance are used.

Botanical classification: *Hibiscus rosa-sinensis* 'Fire Wind'.

Parentage:

*Female, or seed, parent.*—*Hibiscus rosa-sinensis* 'Largo Breeze', disclosed in U.S. Plant Pat. No. 12,869.

*Male or pollen parent.*—Proprietary selection of *Hibiscus rosa-sinensis* identified as code number 2691, not patented.

Propagation:

*Type.*—By vegetative terminal cuttings.

*Time to initiate and develop roots, summer and winter.*—About four weeks at temperatures about 24° C.

*Root description.*—Thick, fibrous; white in color.

*Rooting habit.*—Moderate branching; moderately dense.

Plant description:

*Plant form and growth habit.*—Perennial, evergreen, semi-upright, compact and uniformly mounded plant habit; moderately vigorous to vigorous growth habit.

*Branching habit.*—Freely branching habit with lateral branches potentially develop at every node; pinching enhances lateral branch development; dense and bushy appearance.

*Plant height.*—About 42 cm.

*Plant diameter* (*area of spread*).—About 45 cm.

Lateral branch description:

*Length.*—About 28 cm.

*Diameter.*—About 8 mm.

*Internode length.*—About 1.5 cm.

*Aspect.*—Upright to somewhat outwardly spreading.

*Texture and luster, immature.*—Smooth; glossy.

*Texture and luster, mature.*—Woody and rough; matte.

*Color, immature.*—Close to 187A.

*Color, mature.*—Close to N199B.

Leaf description:

*Arrangement.*—Alternate, single; numerous; symmetrical.

*Length.*—About 7.4 cm.

*Width.*—About 6.7 cm.

*Shape.*—Broadly ovate.

*Apex.*—Acute.

*Base.*—Truncate.

*Margin.*—Crenate.

*Texture and luster, upper and lower surfaces.*—Smooth, glabrous; glossy.

*Venation pattern.*—Pinnate; arcuate.

*Color.*—Developing leaves, upper surface: Darker green than 147A. Developing leaves, lower surface: Close to 147A. Fully expanded leaves, upper surface: Darker green than NN137A; venation, close to NN137A. Fully expanded leaves, lower surface: Close to N137B; venation, close to 146A.

*Petioles.*—Length: About 5.25 cm. Diameter: About 3 mm. Texture and luster, upper and lower surfaces: Smooth, glabrous; slightly glossy. Color, upper and lower surfaces: Close to 187A.

Flower description:

*Flower arrangement and flowering habit.*—Rounded star-shaped single flowers arranged at terminal leaf axils; uniform and freely flowering habit with about three or four flowers per terminal; flowers face mostly upright to outwardly.

*Natural flowering season.*—Plants of the new *Hibiscus* flower naturally during the spring and summer or during periods of warm weather; plants flower year-round in the greenhouse.

*Flower longevity.*—Depending on temperature and water status, flowers typically last about two to three days on the plant; flowers persistent.

*Flower diameter.*—About 10.25 cm.

*Flower length* (*height*).—About 8 cm.

*Flower buds.*—Resistance to abscission during shipping: Plants of the new *Hibiscus* have been observed to resist flower bud drop during shipping. Length: About 2 cm. Diameter: About 1.2 cm. Shape: Ovoid. Texture and luster: Smooth, glabrous; semi-glossy. Color: More green than N137A.

*Petals.*—Arrangement: Corolla consists of a single whorl of five petals that are fused at base; petals imbricate. Length: About 7.25 cm. Width: About 6.5 cm. Shape: Roughly spatulate. Apex: Rounded. Base: Attenuate. Margin: Entire; slightly undulate. Texture and luster, upper surface: Smooth, glabrous; velvety; slightly glossy. Texture and luster, lower surface: Glabrous, veins prominent; glossy. Color: When opening and fully opened, upper surface: Close to 46B; towards the base, close to 53A; venation, similar to lamina, close to 46B and 53A. When opening and fully opened, lower surface: Close to 46B to 46C; venation, close to 46B.

*Sepals*.—Appearance: Five sepals in a single whorl fused into a tubular star-shaped calyx. Length: About 2.5 cm. Width: About 1.2 cm. Shape: Lanceolate. Apex: Sharply acute. Margin: Entire. Texture and luster, upper surface: Smooth, glabrous; waxy; glossy. Texture and luster, lower surface: Smooth, glabrous; matte. Color, upper surface: Close to 146B to 146C. Color, lower surface: Slightly more green than 146A.

*Epicalyx*.—Appearance: About seven in a single whorl fused at base. Length: About 1.6 cm. Width: About 4 mm. Shape: Lanceolate. Apex: Sharply acute. Margin: Entire. Texture and luster, upper and lower surfaces: Smooth, glabrous; matte. Color, upper and lower surfaces: Close to 147A.

*Peduncles*.—Length: About 4 cm. Diameter: About 2 mm. Aspect: Upright to slightly outward. Strength: Strong, flexible. Texture and luster: Smooth, glabrous; semi-glossy. Color: More green than 146A; proximally tinged with close to 187A.

*Reproductive organs*.—Androecium: Stamen number: Numerous, about 50 per flower. Filament length: About 5 mm. Filament color: Close to 46A. Anther shape: Oblong. Anther length: About 1.5 mm. Anther color: Close to 14A. Amount of pollen: Moderate. Pollen color: Close to 14A. Gynoecium: Pistil number: One per flower. Pistil length: About 6.9 cm. Style length: About 5.8 cm. Style texture and luster: Smooth, glabrous; waxy; glossy. Style color: Close to 46A. Stigma appearance: Five-parted, rounded. Stigma color: Close to 53A. Ovary color: Close to 11C to 11D.

*Seeds and fruits*.—To date, seed and fruit production has not been observed on plants of the new *Hibiscus*.

Garden performance: Plants of the new *Hibiscus* have been observed to have good garden performance and to tolerate wind, rain and temperatures ranging from about 1° C. to about 37° C.

Pathogen & pest resistance: To date, plants of the new *Hibiscus* grown under Florida production conditions have not been shown to be resistant to pathogens and pests common to *Hibiscus* plants.

It is claimed:

1. A new and distinct *Hibiscus* plant named 'Fire Wind' as illustrated and described.

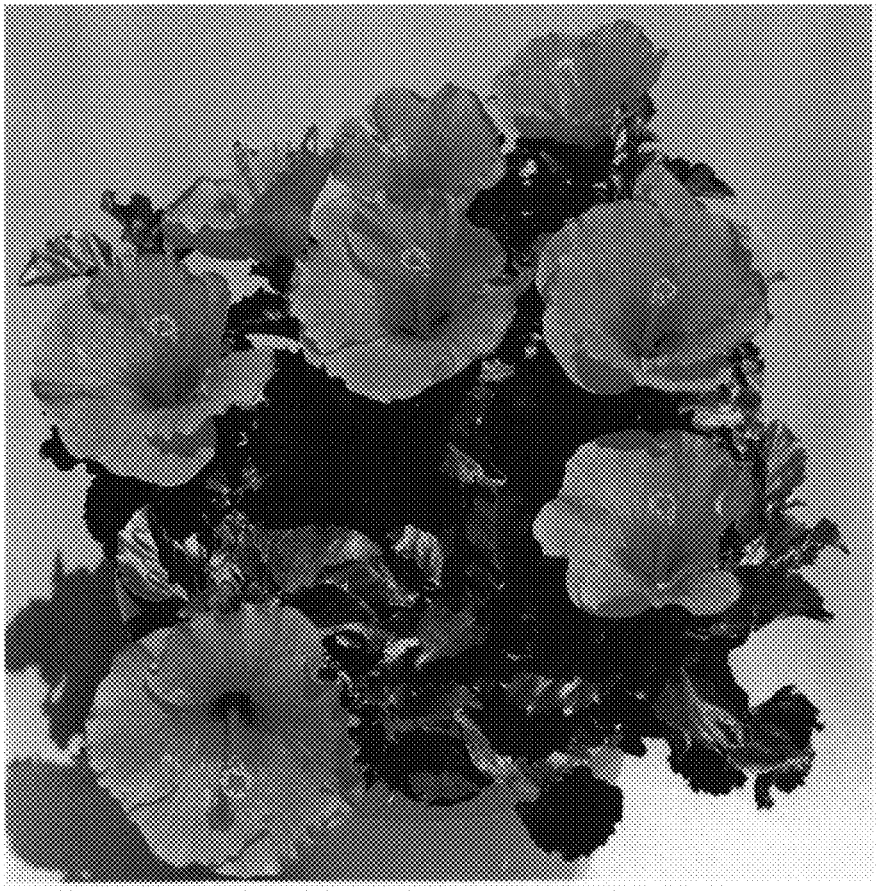

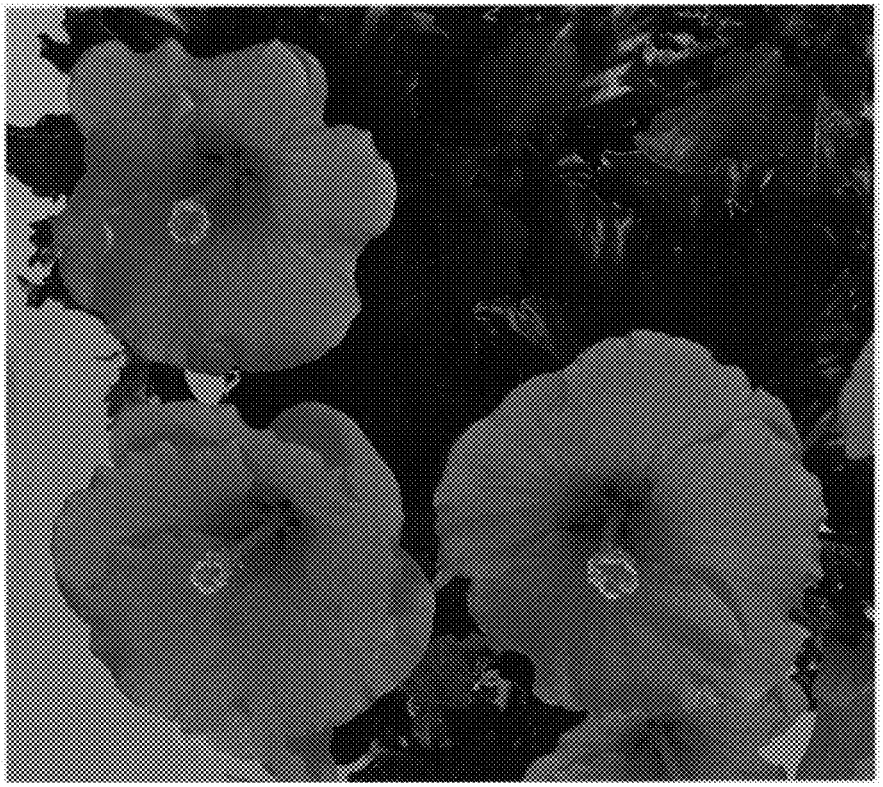

* * * * *